United States Patent
Horst et al.

(10) Patent No.: US 8,274,244 B2
(45) Date of Patent: *Sep. 25, 2012

(54) ACTUATOR SYSTEM AND METHOD FOR EXTENDING A JOINT

(75) Inventors: Robert W. Horst, San Jose, CA (US); Richard R. Marcus, Mountain View, CA (US)

(73) Assignee: Tibion Corporation, Sunnyvale, CA (US)

( * ) Notice: Subject to any disclaimer, the term of this patent is extended or adjusted under 35 U.S.C. 154(b) by 599 days.

This patent is subject to a terminal disclaimer.

(21) Appl. No.: 12/363,577

(22) Filed: Jan. 30, 2009

(65) Prior Publication Data

US 2010/0038983 A1    Feb. 18, 2010

Related U.S. Application Data

(63) Continuation-in-part of application No. 12/191,837, filed on Aug. 14, 2008, now Pat. No. 8,058,823.

(51) Int. Cl.
*H02P 5/00*    (2006.01)
(52) U.S. Cl. .............. 318/34; 318/8; 318/9; 318/14; 318/66; 318/82; 318/83; 310/83
(58) Field of Classification Search .............. 318/8, 9, 318/14, 34, 66, 82, 83; 310/83
See application file for complete search history.

(56) References Cited

U.S. PATENT DOCUMENTS

| | | |
|---|---|---|
| 1,286,482 A | 12/1918 | Yoder |
| 1,366,904 A | 2/1921 | Davis |
| 1,391,290 A | 9/1921 | Welffens |
| 1,513,473 A | 10/1924 | Ackerman |
| 1,739,053 A | 12/1929 | Wilhelm |
| 1,847,720 A | 3/1932 | Marcellis |
| 2,169,813 A | 8/1939 | Parkin |

(Continued)

FOREIGN PATENT DOCUMENTS

EP    1138286 A2    10/2001

(Continued)

OTHER PUBLICATIONS

Advanced Mechatronics Lab (Univ. of Tokyo); Dual Excitation Multiphase Electrostatic Drive (DEMED); http://www.intellect.pe.u-tokyo.ac.jp/research/es_motor/demed_e.html; pp. 1-5; (printed) Nov. 21, 2002.

(Continued)

*Primary Examiner* — Walter Benson
*Assistant Examiner* — Kawing Chan
(74) *Attorney, Agent, or Firm* — Shay Glenn, LLP

(57) ABSTRACT

An actuator system for assisting extension of a biological joint is provided with a motor assembly, a rotary-to-linear mechanism, and an extension stop. The rotary-to-linear mechanism includes a screw that accepts rotational output of the motor assembly, and a nut that cooperates with the screw to convert rotational movement of the screw to linear movement of the nut. The extension stop is driven by linear movement of the nut in an extension direction to cause extension of the biological joint. The motor assembly, the rotary-to-linear mechanism and the extension stop cooperate to allow unpowered flexion of the joint. The system is configured without a flexion stop, and is configured such that the nut cannot drive the joint in a flexion direction. Methods of use are also disclosed.

15 Claims, 12 Drawing Sheets

U.S. PATENT DOCUMENTS

| | | |
|---|---|---|
| 3,059,490 A | 10/1962 | McDuffie |
| 3,200,666 A | 8/1965 | Schrodt et al. |
| 3,358,678 A | 12/1967 | Kultsar |
| 3,398,248 A | 8/1968 | Klauss et al. |
| 3,402,942 A | 9/1968 | Shimano et al. |
| 3,631,542 A | 1/1972 | Potter |
| 3,641,843 A | 2/1972 | Lemmens |
| 3,863,512 A | 2/1975 | Crawley |
| 3,899,383 A | 8/1975 | Schultz et al. |
| 3,925,131 A | 12/1975 | Krause |
| 3,976,057 A | 8/1976 | Barclay |
| 4,474,176 A | 10/1984 | Farris et al. |
| 4,507,104 A | 3/1985 | Clark et al. |
| 4,538,595 A | 9/1985 | Hajianpour |
| 4,549,555 A | 10/1985 | Fraser et al. |
| 4,588,040 A | 5/1986 | Albright, Jr. et al. |
| 4,649,488 A | 3/1987 | Osanai et al. |
| 4,678,354 A | 7/1987 | Olsen |
| 4,679,548 A | 7/1987 | Pecheux |
| 4,691,694 A | 9/1987 | Boyd et al. |
| 4,697,808 A | 10/1987 | Larson et al. |
| 4,731,044 A | 3/1988 | Mott |
| 4,745,930 A | 5/1988 | Confer |
| 4,754,185 A | 6/1988 | Gabriel et al. |
| 4,796,631 A | 1/1989 | Grigoryev |
| 4,801,138 A | 1/1989 | Airy et al. |
| 4,807,874 A | 2/1989 | Little |
| 4,872,665 A | 10/1989 | Chareire |
| 4,878,663 A | 11/1989 | Luquette |
| 4,883,445 A | 11/1989 | Gomoll et al. |
| 4,922,925 A | 5/1990 | Crandall et al. |
| 4,934,694 A | 6/1990 | McIntosh |
| 4,944,713 A | 7/1990 | Salerno |
| 4,953,543 A | 9/1990 | Grim et al. |
| 4,981,116 A | 1/1991 | Trinquard |
| 4,983,146 A | 1/1991 | Charles et al. |
| 5,020,790 A | 6/1991 | Beard et al. |
| 5,052,681 A | 10/1991 | Williams |
| 5,078,152 A | 1/1992 | Bond et al. |
| 5,117,814 A | 6/1992 | Luttrell et al. |
| 5,170,776 A | 12/1992 | Pecheux |
| 5,170,777 A | 12/1992 | Reddy et al. |
| 5,195,617 A | 3/1993 | Clemens |
| 5,203,321 A | 4/1993 | Donovan et al. |
| 5,209,223 A | 5/1993 | McGorry et al. |
| 5,213,094 A | 5/1993 | Bonutti |
| 5,239,222 A | 8/1993 | Higuchi et al. |
| 5,241,952 A | 9/1993 | Ortiz |
| 5,282,460 A | 2/1994 | Boldt |
| 5,303,716 A | 4/1994 | Mason et al. |
| 5,313,968 A | 5/1994 | Logan et al. |
| 5,345,834 A | 9/1994 | Hayashi |
| 5,358,468 A | 10/1994 | Longo et al. |
| 5,378,954 A | 1/1995 | Higuchi et al. |
| 5,395,303 A | 3/1995 | Bonutti et al. |
| 5,421,798 A | 6/1995 | Bond et al. |
| 5,440,945 A | 8/1995 | Penn |
| 5,448,124 A | 9/1995 | Higuchi et al. |
| 5,463,526 A | 10/1995 | Mundt |
| 5,476,441 A | 12/1995 | Durfee et al. |
| 5,509,894 A | 4/1996 | Mason et al. |
| 5,520,627 A | 5/1996 | Malewicz |
| 5,525,642 A | 6/1996 | Cipriano et al. |
| 5,534,740 A | 7/1996 | Higuchi et al. |
| 5,541,465 A | 7/1996 | Higuchi et al. |
| 5,582,579 A | 12/1996 | Chism et al. |
| 5,585,683 A | 12/1996 | Higuchi et al. |
| 5,608,599 A | 3/1997 | Goldman |
| 5,624,390 A | 4/1997 | Van Dyne |
| 5,653,680 A | 8/1997 | Cruz |
| 5,662,594 A | 9/1997 | Rosenblatt |
| 5,662,693 A | 9/1997 | Johnson et al. |
| 5,674,262 A | 10/1997 | Tumey |
| 5,683,351 A | 11/1997 | Kaiser et al. |
| 5,704,440 A | 1/1998 | Urban et al. |
| 5,708,319 A | 1/1998 | Ban et al. |
| 5,728,017 A | 3/1998 | Bellio et al. |
| 5,746,684 A | 5/1998 | Jordan |
| 5,746,704 A | 5/1998 | Schenck et al. |
| 5,755,303 A | 5/1998 | Yamamoto et al. |
| 5,789,843 A | 8/1998 | Higuchi et al. |
| 5,833,257 A | 11/1998 | Kohlheb et al. |
| 5,865,770 A | 2/1999 | Schectman |
| 5,916,689 A | 6/1999 | Collins et al. |
| 5,931,756 A | 8/1999 | Ohsono et al. |
| 5,976,063 A | 11/1999 | Joutras et al. |
| 6,001,075 A | 12/1999 | Clemens et al. |
| 6,033,330 A | 3/2000 | Wong et al. |
| 6,062,096 A | 5/2000 | Lester |
| 6,119,539 A | 9/2000 | Papanicolaou |
| 6,146,341 A | 11/2000 | Sato et al. |
| 6,149,612 A | 11/2000 | Schnapp et al. |
| 6,162,189 A | 12/2000 | Girone et al. |
| 6,183,431 B1 | 2/2001 | Gach, Jr. |
| 6,217,532 B1 | 4/2001 | Blanchard et al. |
| 6,221,032 B1 | 4/2001 | Blanchard et al. |
| 6,290,662 B1 | 9/2001 | Morris et al. |
| 6,314,835 B1 | 11/2001 | Lascelles et al. |
| 6,440,093 B1 | 8/2002 | McEwen et al. |
| 6,472,795 B2 | 10/2002 | Hirose et al. |
| 6,494,798 B1 | 12/2002 | Onogi |
| 6,500,138 B1 | 12/2002 | Irby et al. |
| 6,517,503 B1 | 2/2003 | Naft et al. |
| 6,525,446 B1 | 2/2003 | Yasuda et al. |
| 6,527,671 B2 | 3/2003 | Paalasmaa et al. |
| 6,533,742 B1 | 3/2003 | Gach, Jr. |
| 6,537,175 B1 | 3/2003 | Blood |
| 6,554,773 B1 | 4/2003 | Nissila et al. |
| 6,572,558 B2 | 6/2003 | Masakov et al. |
| 6,599,255 B2 | 7/2003 | Zhang |
| 6,659,910 B2 | 12/2003 | Gu et al. |
| 6,666,796 B1 * | 12/2003 | MacCready, Jr. ............... 482/51 |
| 6,689,075 B2 | 2/2004 | West |
| 6,694,833 B2 | 2/2004 | Hoehn et al. |
| 6,709,411 B1 | 3/2004 | Olinger |
| 6,796,926 B2 | 9/2004 | Reinkensmeyer et al. |
| 6,805,677 B2 | 10/2004 | Simmons |
| 6,821,262 B1 | 11/2004 | Muse et al. |
| 6,827,579 B2 | 12/2004 | Burdea et al. |
| 6,836,744 B1 | 12/2004 | Asphahani et al. |
| 6,872,187 B1 | 3/2005 | Stark et al. |
| 6,878,122 B2 | 4/2005 | Cordo |
| 6,936,994 B1 | 8/2005 | Gimlan |
| 6,966,882 B2 | 11/2005 | Horst |
| 7,041,069 B2 | 5/2006 | West |
| 7,124,321 B2 | 10/2006 | Garnett et al. |
| 7,137,938 B2 | 11/2006 | Gottlieb |
| 7,171,331 B2 | 1/2007 | Vock et al. |
| 7,190,141 B1 | 3/2007 | Ashrafiuon et al. |
| 7,192,401 B2 | 3/2007 | Saalasti et al. |
| 7,239,065 B2 | 7/2007 | Horst |
| 7,252,644 B2 | 8/2007 | Dewald et al. |
| 7,309,320 B2 | 12/2007 | Schmehl |
| 7,324,841 B2 | 1/2008 | Reho et al. |
| 7,365,463 B2 | 4/2008 | Horst et al. |
| 7,410,471 B1 | 8/2008 | Campbell et al. |
| 7,416,537 B1 | 8/2008 | Stark et al. |
| 7,431,707 B2 | 10/2008 | Ikeuchi |
| 7,458,922 B2 | 12/2008 | Pisciottano |
| 7,537,573 B2 | 5/2009 | Horst |
| 7,559,909 B2 | 7/2009 | Katoh et al. |
| 7,578,799 B2 | 8/2009 | Thorsteinsson et al. |
| 7,648,436 B2 | 1/2010 | Horst et al. |
| 7,731,670 B2 | 6/2010 | Aguirre-Ollinger et al. |
| 7,833,178 B2 | 11/2010 | Lee et al. |
| 7,880,345 B2 * | 2/2011 | Hoffmann et al. ......... 310/12.13 |
| 7,998,092 B2 | 8/2011 | Avni et al. |
| 2001/0029343 A1 | 10/2001 | Seto et al. |
| 2002/0128552 A1 * | 9/2002 | Nowlin et al. ................ 600/427 |
| 2003/0104886 A1 | 6/2003 | Gajewski |
| 2003/0120183 A1 | 6/2003 | Simmons |
| 2003/0195638 A1 * | 10/2003 | Kajitani et al. ................ 623/64 |
| 2003/0212356 A1 | 11/2003 | Scorvo |
| 2004/0015112 A1 | 1/2004 | Salutterback et al. |
| 2004/0049139 A1 | 3/2004 | Craciunescu |
| 2004/0054311 A1 | 3/2004 | Sterling |
| 2004/0078091 A1 | 4/2004 | Elkins |

| | | | |
|---|---|---|---|
| 2004/0106881 | A1 | 6/2004 | McBean et al. |
| 2005/0014600 | A1* | 1/2005 | Clauson .......................... 477/2 |
| 2005/0085346 | A1 | 4/2005 | Johnson |
| 2005/0085353 | A1 | 4/2005 | Johnson |
| 2005/0101887 | A1 | 5/2005 | Stark et al. |
| 2005/0151420 | A1 | 7/2005 | Crombez et al. |
| 2005/0173994 | A1* | 8/2005 | Pfister et al. .................... 310/12 |
| 2005/0210557 | A1 | 9/2005 | Falconer |
| 2005/0221926 | A1 | 10/2005 | Naude |
| 2005/0245849 | A1 | 11/2005 | Cordo |
| 2005/0251067 | A1 | 11/2005 | Terry |
| 2005/0273022 | A1 | 12/2005 | Diaz et al. |
| 2006/0004265 | A1 | 1/2006 | Pulkkinen et al. |
| 2006/0069336 | A1 | 3/2006 | Krebs et al. |
| 2006/0132069 | A1 | 6/2006 | Hemphill et al. |
| 2006/0157010 | A1* | 7/2006 | Moriwaki et al. ......... 123/90.13 |
| 2006/0206045 | A1 | 9/2006 | Townsend et al. |
| 2006/0249315 | A1 | 11/2006 | Herr et al. |
| 2006/0251179 | A1 | 11/2006 | Ghoshal |
| 2006/0293624 | A1 | 12/2006 | Enzerink et al. |
| 2007/0015611 | A1 | 1/2007 | Noble et al. |
| 2007/0055163 | A1 | 3/2007 | Asada et al. |
| 2007/0155557 | A1 | 7/2007 | Horst et al. |
| 2007/0155558 | A1 | 7/2007 | Horst et al. |
| 2007/0155560 | A1 | 7/2007 | Horst et al. |
| 2007/0155588 | A1 | 7/2007 | Stark et al. |
| 2007/0162152 | A1 | 7/2007 | Herr et al. |
| 2007/0173747 | A1 | 7/2007 | Knotts |
| 2007/0225620 | A1 | 9/2007 | Carignan et al. |
| 2007/0265534 | A1 | 11/2007 | Martikka et al. |
| 2007/0270265 | A1 | 11/2007 | Miller et al. |
| 2007/0287928 | A1 | 12/2007 | Kiviniemi et al. |
| 2008/0039731 | A1 | 2/2008 | McCombie et al. |
| 2008/0097269 | A1 | 4/2008 | Weinberg et al. |
| 2008/0195005 | A1 | 8/2008 | Horst et al. |
| 2008/0200994 | A1 | 8/2008 | Colgate et al. |
| 2008/0234608 | A1 | 9/2008 | Sankai |
| 2009/0007983 | A1 | 1/2009 | Healy |
| 2009/0036804 | A1 | 2/2009 | Horst |
| 2009/0048686 | A1 | 2/2009 | Ikeuchi et al. |
| 2009/0131839 | A1 | 5/2009 | Yasuhara |
| 2009/0171469 | A1 | 7/2009 | Thorsteinsson et al. |
| 2009/0204038 | A1 | 8/2009 | Smith et al. |
| 2009/0260426 | A1 | 10/2009 | Lieberman et al. |
| 2009/0306548 | A1 | 12/2009 | Bhugra et al. |
| 2010/0039052 | A1 | 2/2010 | Horst et al. |
| 2010/0049102 | A1 | 2/2010 | Yasuhara |
| 2010/0113986 | A1 | 5/2010 | Ashihara et al. |
| 2010/0114329 | A1 | 5/2010 | Casler et al. |
| 2010/0125229 | A1 | 5/2010 | Rudolph et al. |
| 2010/0234775 | A1 | 9/2010 | Yasuhara et al. |
| 2010/0280628 | A1 | 11/2010 | Sankai |
| 2010/0318006 | A1 | 12/2010 | Horst |

FOREIGN PATENT DOCUMENTS

| | | |
|---|---|---|
| EP | 1410780 A1 | 4/2004 |
| JP | 63-136978 A | 6/1988 |
| JP | 02-275162 A | 11/1990 |
| JP | 04-104180 A | 4/1992 |
| JP | 05-260766 | 10/1993 |
| JP | 06-038551 A | 2/1994 |
| JP | 07-274540 A | 10/1995 |
| JP | 08-033360 A | 2/1996 |
| JP | 08-149858 | 6/1996 |
| JP | 08-154304 A | 6/1996 |
| JP | 09-261975 A | 10/1997 |
| WO | WO 90/11049 A1 | 10/1990 |
| WO | WO 2005/057054 A1 | 6/2005 |
| WO | WO 2007/027673 A2 | 3/2007 |
| WO | WO 2007/041303 A2 | 4/2007 |

OTHER PUBLICATIONS

Advanced Mechatronics Lab (Univ. of Tokyo); High-power electrostatic motor; http://www.intellect.pe.u-tokyo.ac.jp/research/es_motor/es_motor_e.html; pp. 1-2; (printed) Nov. 21, 2002.
Advanced Mechatronics Lab (Univ. of Tokyo); Pulse driven induction electrostatic motor; http://www.intellect.pe.u-tokyo.ac.jp/research/es_motor/pim_e.html; pp. 1-5; (printed) Nov. 21, 2002.
Asel (Univ. of Delaware); Powered orthosis project; http://www.asel.udel.edu/robotics/orthosis/orthosis.html, 1 pg.; (update) Jan. 17, 1999.
British Tech. Group; Demonstration of energy saving in vehicles by integrating an infinitely variable transmission with an optimized petrol engine; prj. No. TR/00087/92; pp. 1-19; (version) Jul. 15, 1998.
Coronel et al; The Coronel effect positively infinitely variable transmission; U.C. Davis; No. 04CVT-51; pp. 1-8; 2004.
Fitch, C. J.; Development of the electrostatic clutch; IBM Journal; pp. 49-56; Jan. 1957.
Frank, Andrew; Engine optimization concepts for CVT-hybrid system to obtain the best performance and fuel efficiency; U.C. Davis; No. 04CVT-56; pp. 1-12; 2004.
Gongola et al.; Design of a PZT-actuated proportional drum brake; IEEE ASME Trans. on Mech.; vol. 4; No. 4; pp. 409-416; Dec. 1999.
Howard Leitch, PPT Ltd.; Waveform Gearing; Motion System Design; pp. 33-35; Nov. 2002.
James et al.; Increasing power density in a full toroidal variator; 3rd Int'l. IIR-Symposium; Innovative Automotive Transmission; pp. 1-11; Dec. 2004.
Kawamoto et al.; Power assist system HAL-3 for GAIT disorder person; ICCHP 2002; LNCS 2398; pp. 196-203; 2002.
Kim et al.; On the energy efficiency of CVT-based mobile robots; Proc. 2000 IEEE; Int. Conf. on Robotics & Automation; pp. 1539-1544; San Francisco, CA; Apr. 2000.
Kluger et al.; An overview of current automatic, manual and continuously variable transmission efficiencies and their projected future improvements; Int. Congress and Expo. (No. 1999-1-1259); pp. 1-6; Detroit, MI; Mar. 1-4, 1999.
Krebs et al.; A paradigm shift for rehabilitation robotics; Eng. in Medicine and Biology Magazine, IEEE; vol. 27; Issue 4; pp. 61-70; Jul. 2008.
Misuraca et al.; Lower limb human enhancer; Int. Mech. Eng. Conf. and Expo.; New York, NY; pp. 1-7; Nov. 11-16, 2001.
Niino et al.; Electrostatic artificial muscle: compact, high-power linear actuators with multiple-layer structures; Proc. IEEE Workshop on Micro Electro Mechanical Systems; Oiso, Japan; pp. 130-135; Jan. 1994.
Nugent, James; Design and performance of an exponential roller gear continuously variable transmission with band clutches; U.C. Davis; No. 04CVT-18; pp. 1-8; 2004.
Ohhashi, Toshio et al.; Human perspiration measurement; Physiological Measurement; vol. 19; pp. 449-461; 1998.
Otto Bock Health Care; (3C100 C-Leg® System) Creating a new standard for prosthetic control; http://www.ottobockus.com/products/op_lower_cleg.asp; pp. 1-2; (printed) Nov. 22, 2002.
Otto Bock Health Care; (3C100 C-Leg® System) New generation leg system revolutionizes lower limb prostheses; http://www.ottobockus.com/products/op_lower_cleg4.asp; pp. 1-2; (printed) Nov. 22, 2002.
Patras et al.; Electro-rheological fluids in the design of clutch systems for robotic applications; IEEE; pp. 554-558; Nov. 11-13, 1992.
Powell et al.; Computer model for a parallel hybrid electric vehicle (PHEV) with CVT; Proc. AACC; pp. 1011-1015; Chicago, IL; Jun. 2000.
Shastri et al.; Comparison of energy consumption and power losses of a conventionally controlled CVT with a servo-hydraulic controlled CVT and with a belt and chain as the torque transmitting element; U.C. Davis; No. 04CVT-55; pp. 1-11; 2004.
Shriner's Hospitals; Your new orthosis; http://www.shrinershq.org/patientedu/orthosis.html; pp. 1-3; (printed) Nov. 22, 2002.
Takaki et al; Load-sensitive continuously variable transmission for powerful and inexpensive robot hands; IEEE; pp. 45-46; 2004.
Takesue et al.; Development and experiments of actuator using MR fluid; IEEE; pp. 1838-1843; 2000.

Townsend Design; Functional Bracing Solutions (AIR Townsend & Ultra AIR); http://www.townsenddesign.com/air.html; 2 pgs; (printed) Nov. 21, 2002.

Townsend Design; Functional Knee Bracing Solutions; http://www.townsenddesign.com/functional.html; pp. 1; (printed) Nov. 21, 2002.

Townsend Design; Patented Motion Hinge (Planes of Motion); http://www.townsenddesign.com/motion.html; pp. 1; (printed) Nov. 21, 2002.

Trimmer et al.; An operational harmonic electrostatic motor; IEEE; pp. 13-16; 1989.

Smith et al., U.S. Appl. No. 12/471,299 entitled "Therapy and mobility assistance system," filed May 22, 2009.

Bhugra, Kern; U.S. Appl. No. 12/363,567 entitled "System and method for controlling the joint motion of a user based on a measured physiological property," filed Jan. 30, 2009.

Horst et al., U.S. Appl. No. 12/703,067 entitled "Foot pad device and method of obtaining weight data," filed Feb. 9, 2010.

Horst, Robert W.; U.S. Appl. No. 13/290,980 entitled "Intention-based therapy device and method," filed Nov. 7, 2011.

Smith et a.; U.S. Appl. No. 13/274,109 entitled "Multi-fit orthotic and mobility assistance apparatus," filed Oct. 14, 2011.

* cited by examiner

ACTUATOR SYSTEM AND METHOD FOR EXTENDING A JOINT

CROSS-REFERENCE TO RELATED APPLICATIONS

This application is a continuation-in-part of prior application Ser. No. 12/191,837 entitled "Actuator System With a Multi-Motor Assembly For Extending and Flexing a Joint" filed 14 Aug. 2008, which is incorporated in its entirety by this reference.

TECHNICAL FIELD

This invention relates generally to the actuator field, and more specifically to a new and useful actuator system with a motor assembly in the actuator field.

BACKGROUND

Motors and actuators are used in a wide variety of applications. Many applications, including robotics and active orthotics, require characteristics similar to human muscles. The characteristics include the ability to deliver high force at a relatively low speed and to allow free-movement when power is removed, thereby allowing a limb to swing freely during portions of the movement cycle. This may call for an actuator that can supply larger forces at slower speeds and smaller forces at higher speeds, or a variable ratio transmission (VRT) between the primary driver input and the output of an actuator.

VRTs have been conventionally implemented as Continuously Variable Transmissions (CVTs). The underlying principle of most previous CVTs is to change the ratio of one or more gears by changing the diameter of the gear, changing the place where a belt rides on a conical pulley, or by coupling forces between rotating disks with the radius of the intersection point varying based on the desired ratio. Prior art CVTs have drawbacks in efficiency and mechanical complexity.

Motors have been used in a variety of applications, but typically a single motor is directly or indirectly coupled to provide motion for each output direction. Use of a single motor limits the speed/torque range or requires the extra cost and complexity of a transmission between the motor and output. Thus, there is a need in the actuator field to create a new and useful actuator system that can supply larger forces at slower speeds and smaller forces at higher speeds, but that minimizes or avoids the disadvantages of the conventional CVTs. This invention provides such a new and useful actuator system.

DESCRIPTION OF THE PREFERRED EMBODIMENTS

The following description of the preferred embodiments of the invention is not intended to limit the invention to these preferred embodiments, but rather to enable any person skilled in the art of actuator systems to make and use this invention.

Figure 1:
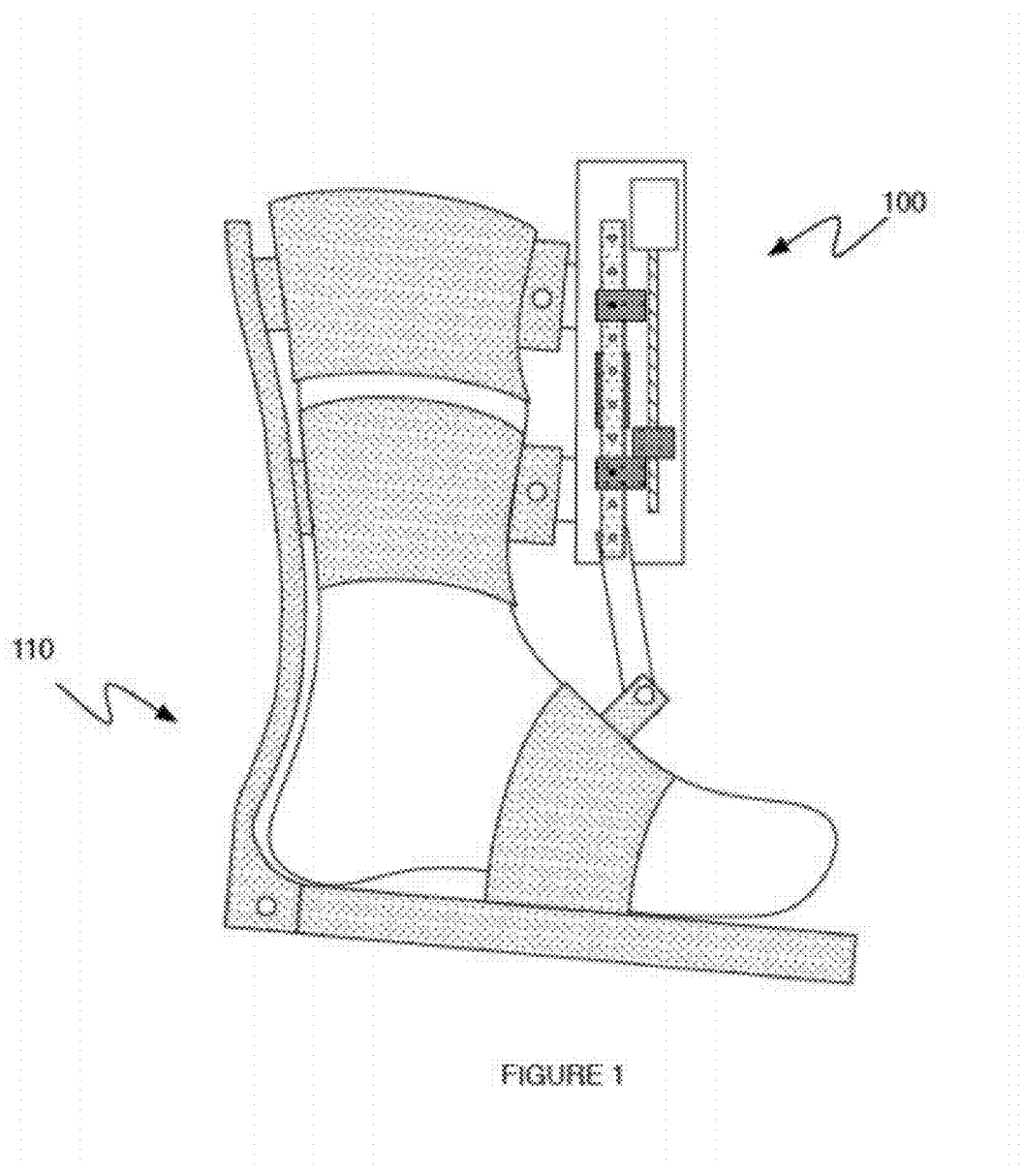
FIG. 1 is a schematic of the actuator system of the preferred embodiment in an orthotic that extends and flexes a joint of a user.
Figure 2:
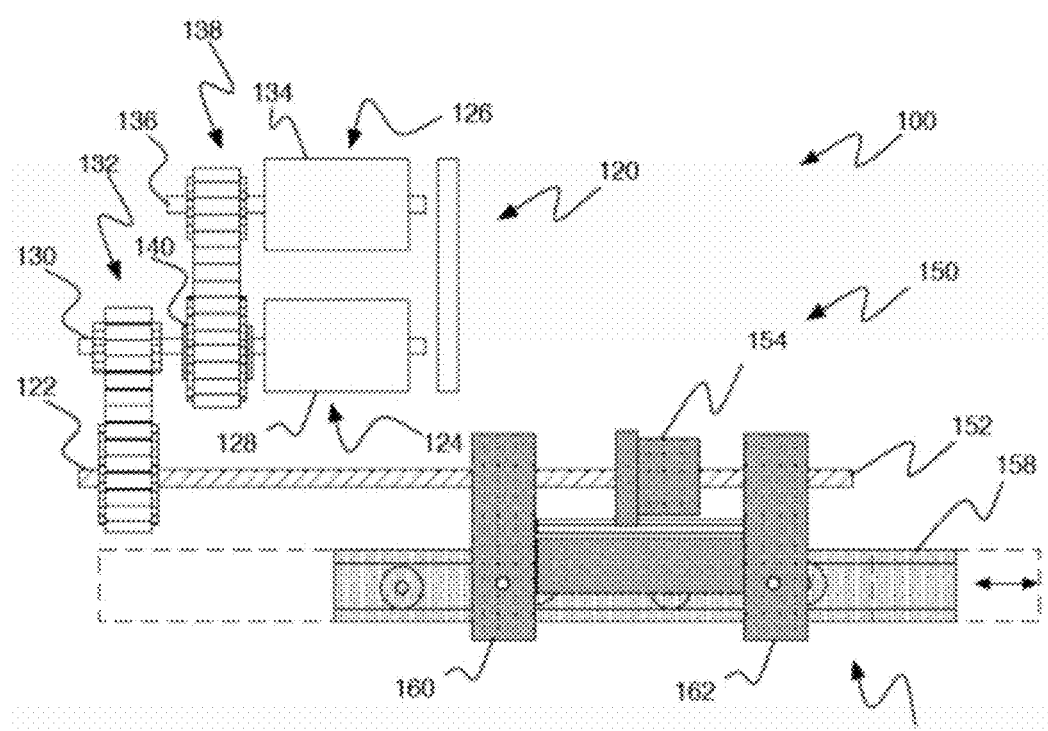
FIG. 2 is a schematic of the actuator system of the preferred embodiment, with the first variation of the multi-motor assembly and with both the extension stop and the flexion stop of the rotary-to-linear mechanism in the force positions.

As shown in FIGS. 1 and 2, the actuator system 100 of the preferred embodiments for extending and flexing a joint 110 of a user includes a multi-motor assembly 120 for providing a rotational output, a rotary-to-linear mechanism 150 for converting the rotational output from the multi-motor assembly 120 into a linear motion that ultimately extends and flexes the joint, and a controller for operating the actuator system 100 in several operational modes. The multi-motor assembly 120 preferably combines power from two different sources, such that the multi-motor assembly 120 can supply larger forces at slower speeds ("Low Gear") and smaller forces at higher speeds ("High Gear"). The actuator has been specifically designed for extending and flexing a joint 110 (such as an ankle, a knee, an elbow, or a shoulder) of a human or robot. The actuator system 100 may, however, be used to move any suitable object through any suitable movement (linear, rotational, or otherwise).

1. Multi-motor Assembly

As shown in FIG. 2, the multi-motor assembly 120 of the preferred embodiments functions to provide rotational output to the rotary-to-linear mechanism 150. The multi-motor assembly 120 includes a drive shaft 122, a first motor subsystem 124, and a second motor subsystem 126. The drive shaft 122 functions to deliver the rotational output from the multi-motor assembly 120. The first motor subsystem 124 functions to provide a component of the rotational output of the multi-motor assembly 120. The first motor subsystem 124 includes a first motor 128, a first output shaft 130, and a first transmission 132. The second motor subsystem 126 functions to provide another component of the rotational output of the multi-motor assembly 120. The second motor subsystem 126 includes a second motor 134, a second output shaft 136, and a second transmission 138.

The first motor 128 of the first motor subsystem 124 functions to provide a first source of power, and the first output shaft 130 functions to deliver this power to the other elements of the first motor subsystem 124. The first motor 128 is preferably a three phase brushless electric motor with an outer rotor and seven pole pairs. The first motor 128, which is preferably supplied by Hyperion under the model number G2220-14, has a peak current of 35 A and a peak power of 388 W. The first motor 128 may, of course, be a different type with different specifications and parameters depending on the design of the actuator system 100.

The first transmission 132 of the first motor subsystem 124 functions to transmit the power from the first output shaft 130 to the drive shaft 122. The first transmission 132 preferably includes two pulleys (one mounted on the first output shaft 130 and one mounted on the drive shaft 122) and a belt or chain connecting the two pulleys. The first transmission 132 may alternatively include gears or any other suitable device or method that transmits the power from the first output shaft 130 to the drive shaft 122. The first transmission 132 also preferably functions to define a first gear ratio of the rotation of the drive shaft 122 to the rotation of the first output shaft 130. In the preferred embodiment, the pulley (or gear) mounted to the first output shaft 130 is smaller than the pulley (or gear) mounted to the drive shaft 122, such that the first gear ratio is less than 1:1 (e.g., 1:4). In alternative embodiments, the first gear ratio may be 1:1 or may be greater than 1:1 (e.g., 4:1) depending on the design of the actuator system 100.

The second motor 134 of the second motor subsystem 126 functions to provide a second source of power, and the second output shaft 136 functions to deliver this power to the other elements of the second motor subsystem 126. The second motor 134, like the first motor 128, is preferably a three phase brushless electric motor with an outer rotor and seven pole pairs. The second motor 134, which is preferably supplied by Hyperion under the model number G2220-14, has a peak current of 35 A and a peak power of 388 W. The second motor 134 is preferably identical to the first motor 128 in design and performance characteristics, which functions to reduce part count and manufacturing complexity. The second motor 134 may, however, be a different type with different specifications and parameters depending on the design of the actuator system 100. The second output shaft 136 functions to deliver the power of the second motor 134 to the other elements of the second motor subsystem 126.

The second transmission 138 of the second motor subsystem 126 functions to transmit the power from the second output shaft 136 to the drive shaft 122. The second transmission 138 preferably includes two pulleys (one mounted on the second output shaft 136 and one mounted on the drive shaft 122) and a belt or chain connecting the two pulleys. The second transmission 138 may alternatively include gears or any other suitable device or method that transmits the power from the second output shaft 136 to the drive shaft 122. The second transmission 138 also preferably functions to at least partially define the second gear ratio of the rotation of the drive shaft 122 to the rotation of the second output shaft 136. In the preferred embodiment, the pulley (or gear) mounted to the second output shaft 136 is smaller than the pulley (or gear) mounted to the drive shaft 122, such that the second gear ratio is less than 1:1 (e.g., 1:4). In alternative embodiments, the second gear ratio may be 1:1 or may be greater than 1:1 (e.g., 4:1) depending on the design of the actuator system 100.

The power from the first motor subsystem 124 and the power from the second motor subsystem 126 preferably have different characteristics, such that the multi-motor assembly 120 can supply larger forces at slower speeds ("Low Gear") and smaller forces at higher speeds ("High Gear"). This may be accomplished by using different motors in the first motor subsystem 124 and the second motor subsystem 126. In the preferred embodiment, however, this is accomplished by using identical motors, but with transmissions that define different gear ratios for the first motor subsystem 124 and the second motor subsystem 126. The second gear ratio is preferably lower than the first gear ratio, but the actuator system 100 may be re-arranged such that the second gear ratio is higher than the first gear ratio.

The second transmission 138 of the second motor subsystem 126 preferably connects the second output shaft 136 to the first output shaft 130. With this arrangement, the power from the second motor 134 is transmitted through both the second transmission 138 and the first transmission 132 before reaching the drive shaft 122. Thus, the second transmission 138 and the first transmission 132 cooperatively define the second gear ratio. The effective gear ratio from motor 134 to the drive shaft 122 is a product of the first transmission 132 and the second transmission 138. For example, if the gear ratios of both the first transmission 132 and the second transmission 138 were 1:3, then the effective gear ratio from motor 134 to the drive shaft 122 would be 1:9. By leveraging the first transmission 132, this variation provides a compact form factor. Using the example, the system would be able to provide an effective gear ratio of 1:9 without the need for a large pulley or gear system.

Figure 3:
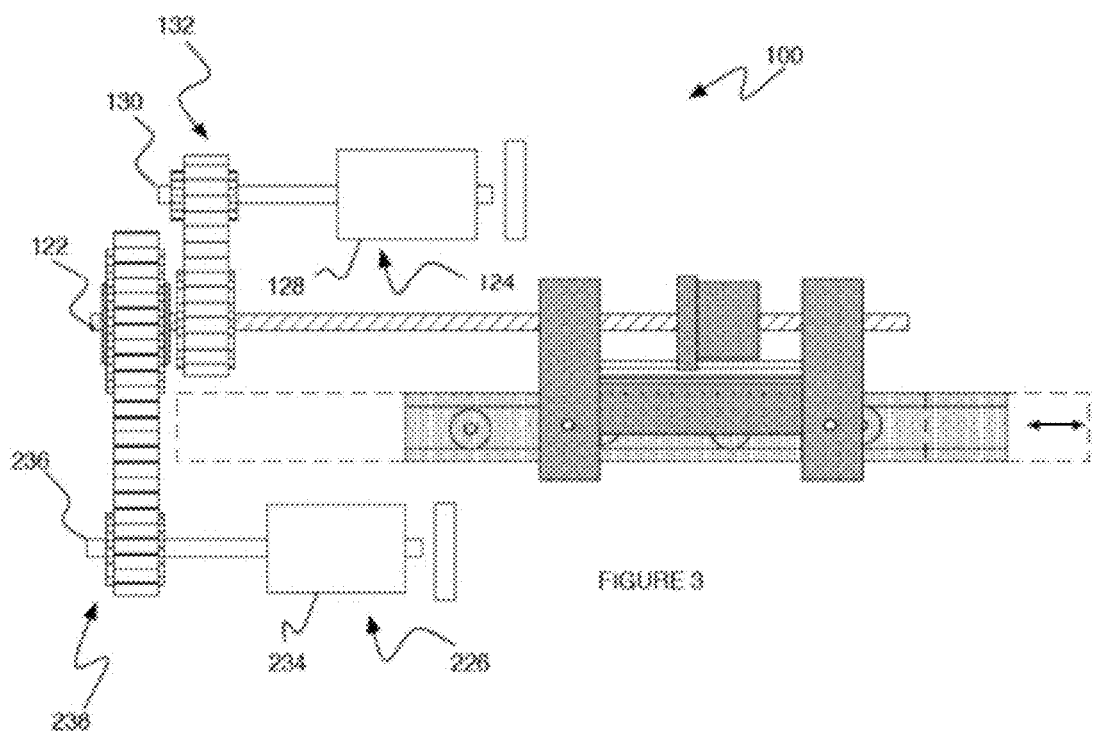
FIG. 3 is a schematic of the actuator system of the preferred embodiment, with the second variation of the multi-motor assembly.

As shown in FIG. 3, a second transmission 238 of a variation of the second motor subsystem 226 connects the second output shaft 236 to the drive shaft 122. In this variation, the power from the second motor 234 is transmitted through only the second transmission 238 before reaching the drive shaft 122 (and, thus, the second transmission 238 defines the second gear ratio). By separately connecting the first motor 128 and the second motor 234 to the drive shaft 122, the first gear ratio and the second gear ratio may be specifically tailored for the actuator system 100.

As shown in FIG. 2, the multi-motor assembly 120 of the preferred embodiment also includes a one-way clutch 140 located between the second motor 134 and the drive shaft 122. The one-way clutch 140 functions to facilitate the following motor modes:

High Gear motor mode—the first motor subsystem 124 provides powers in a first direction without spinning the second output shaft 136 and imparting drag from the second motor subsystem 126, Low Gear motor mode—the second motor subsystem 126 provides power in the first direction (with drag from the first motor subsystem 124), Combined motor mode—the first motor subsystem 124 and the second motor subsystem 126 provide power in the first direction, and High Gear motor mode—the first motor subsystem 124 provides power in an opposite direction (with drag from the second motor subsystem 126).

In a first variation of the multi-motor assembly 120, as introduced above, the one-way clutch 140 is preferably located within the second transmission 138 and, more specifically, in the pulley mounted on the first output shaft 130. In other variations, the one-way clutch 140 may be mounted in any suitable location between the second motor 134 and the drive shaft 122.

The multi-motor assembly 120 of the preferred embodiment also includes a power source (not shown). The power source is preferably six lithium polymer battery cells, supplied by Emerging Power under the model number 603462H1. The battery cells are preferably arranged in both series and parallel (3S2P) to provide a voltage of 11.1V (nominal) and a capacity of 2640 maH. The power source may, however, be any suitable type, including both power supplied by the power grid and other portable sources (e.g., fuel cells), depending on the design of the actuator system 100.

2. Rotary-to-linear Mechanism

The rotary-to-linear mechanism 150 of the preferred embodiment functions to convert the rotational output from the multi-motor assembly 120 into a linear movement that ultimately extends and flexes the joint of the user. In the preferred embodiment, the rotary-to-linear mechanism 150 includes a ball screw 152 that accepts the rotational output of the multi-motor assembly 120 and a ball nut 154 that connects to the ball screw 152 and cooperates with the ball screw 152 to convert rotational movement of the ball screw 152 to linear movement of the ball nut 154. The drive shaft 122 of the multi-motor assembly 120 and the ball screw 152 of the rotary-to-linear mechanism 150 are preferably different sections of the same shaft. One section includes a pulley (or gear) from the first transmission 132, while another section includes a semi-circular, helical groove of the ball screw 152. The drive shaft 122 and the ball screw 152 may, however, be separate shafts connected in any suitable manner, such as through a pulley or gear arrangement. In alternative embodiments, the rotary-to-linear mechanism 150 may include any suitable device or method that converts the rotational output from the multi-motor assembly 120 into an extension and flexion of the joint.

The rotary-to-linear mechanism 150 of the preferred embodiment also includes a linear slide 156 with a moving rail 158 that moves in a flexion direction and an extension direction. The linear slide 156 functions to provide a supported structure when the joint is fully flexed, and a compact structure when the joint is fully extended. The linear slide 156 preferably includes stationary wheels and moving wheels, but may alternatively include any suitable device or method to allow the moving rail 158 to move in the flex and extended directions.

Figure 4A:
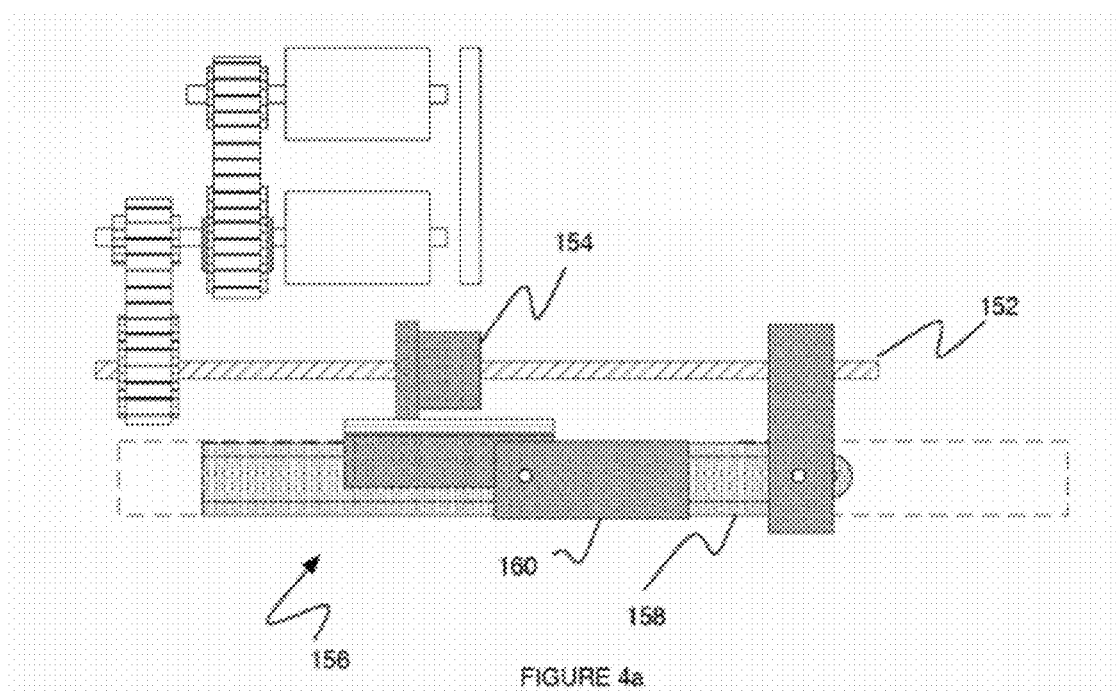
FIG. 4a is a schematic of the actuator system of the preferred embodiment, with the extension stop in the pass position.

As shown in FIGS. 2 and 4a, the moving rail 158 of the linear slide 156 preferably includes an extension stop 160, which functions to translate linear movement of the ball nut 154 in an extension direction into an extension of the joint. In the preferred embodiment, the extension stop 160 is movable between a force position (shown in FIG. 2) that allows the ball nut 154 to apply force against the extension stop 160, and a pass position (shown in FIG. 4a) that prevents the ball nut 154 from applying force against the extension stop 160. In the force position, the extension stop 160 preferably applies a symmetric force to the ball nut 154 to avoid damaging or obstructing the ball nut. The extension stop 160 is preferably U-shaped and pivotally mounted on the moving rail 158, but may alternatively be shaped and mounted in any manner to allow movement from the force position to the pass position. In an alternative embodiment, the extension stop 160 may be permanently (or semi-permanently) fixed or fastened in the force position.

Figure 4B:
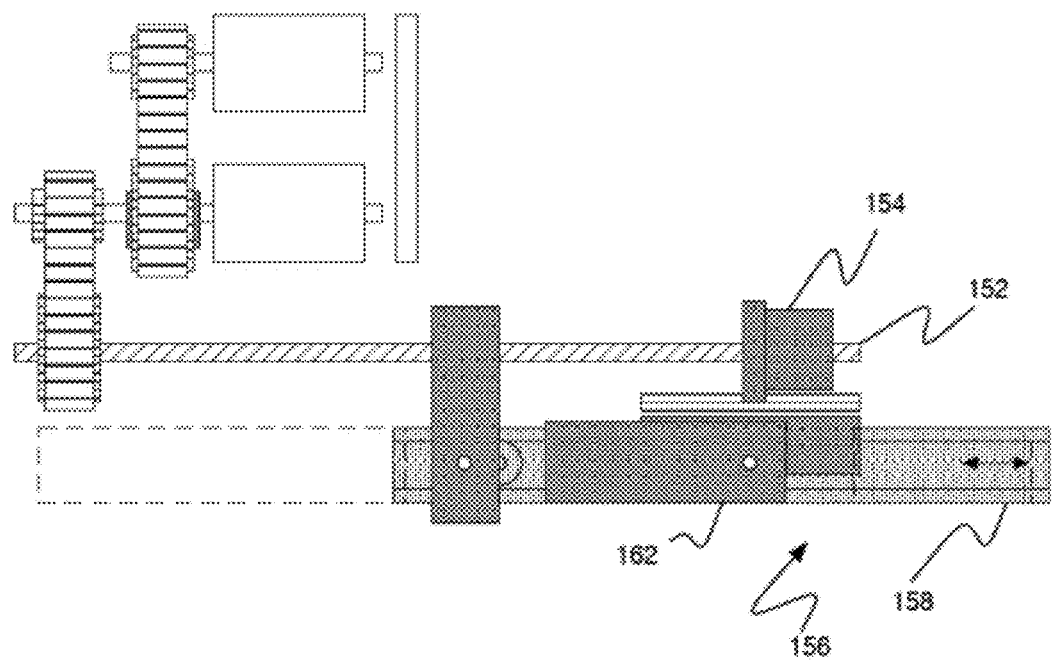
FIG. 4b is a schematic of the actuator system of a first variation, with the flexion stop in the pass position.

In a first variation, as shown in FIGS. 2 and 4b, the moving rail 158 of the linear slide 156 also includes a flexion stop 162, which functions to translate linear movement of the ball nut 154 in a flexion direction into a flexion of the joint. The flexion stop 162 is preferably movable between a force position (shown in FIG. 2) that allows the ball nut 154 to apply force against the flexion stop 162, and a pass position (shown in FIG. 4b) that prevents the ball nut 154 from applying force against the flexion stop 162. Like the extension stop 160, the flexion stop 162 preferably applies a symmetric force to the ball nut 154 when in the force position, to avoid damaging or obstructing the ball nut. The flexion stop 162, like the extension stop 160, is preferably U-shaped and pivotally mounted on the moving rail 158. In another variation, the flexion stop 162 is pivotally mounted on the extension stop 160 (as shown in FIG. 4d) to be movable between a force position (as shown in FIGS. 4d and 4e) and a pass position. The flexion stop 162 may, however, alternatively be shaped and mounted in any manner to allow movement from the force position to the pass position. The flexion stop 162 may alternatively be permanently (or semi-permanently) fixed or fastened in the force position.

Figure 4C:
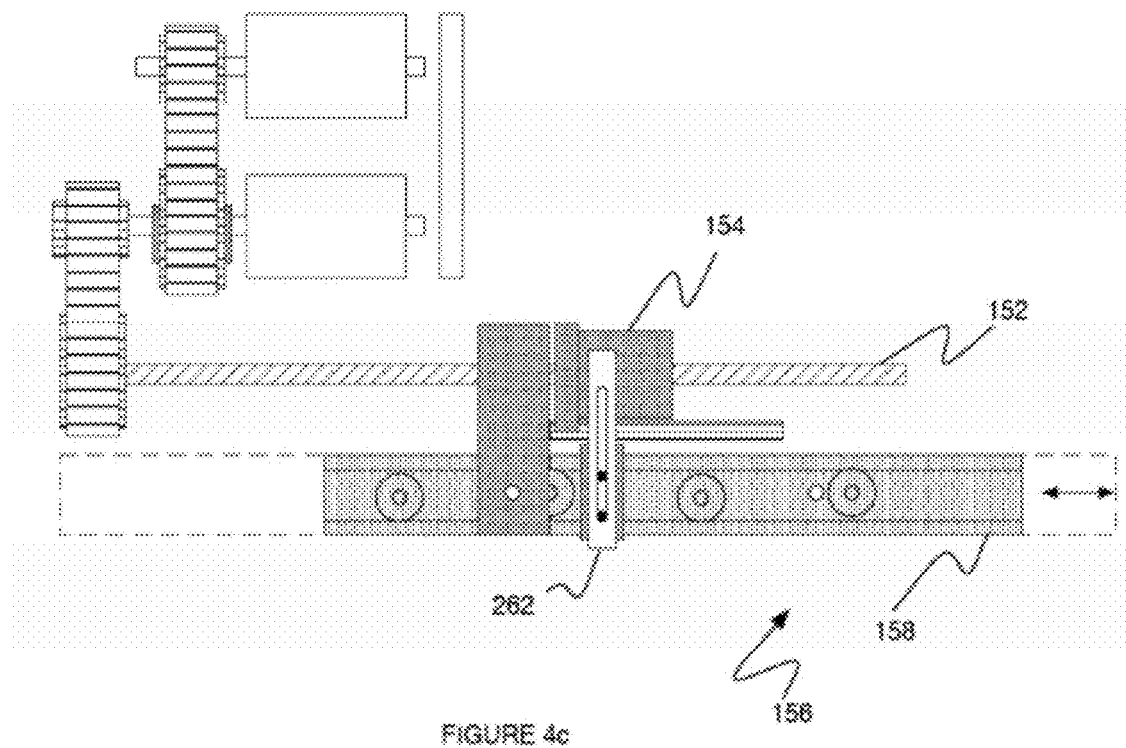
FIG. 4c is a schematic of the actuator system of a second variation, with the latch in the engaged position.
Figure 4D:
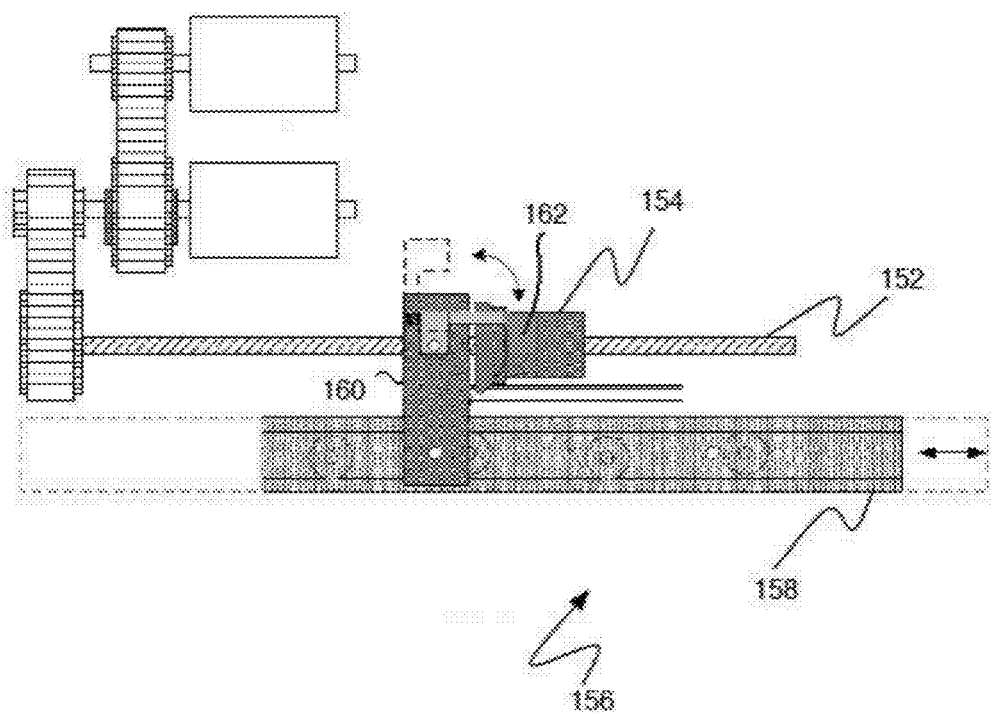
FIG. 4d is a schematic of the actuator system of a third variation with both the flexion stop and extension stop in the force positions.
Figure 4E:
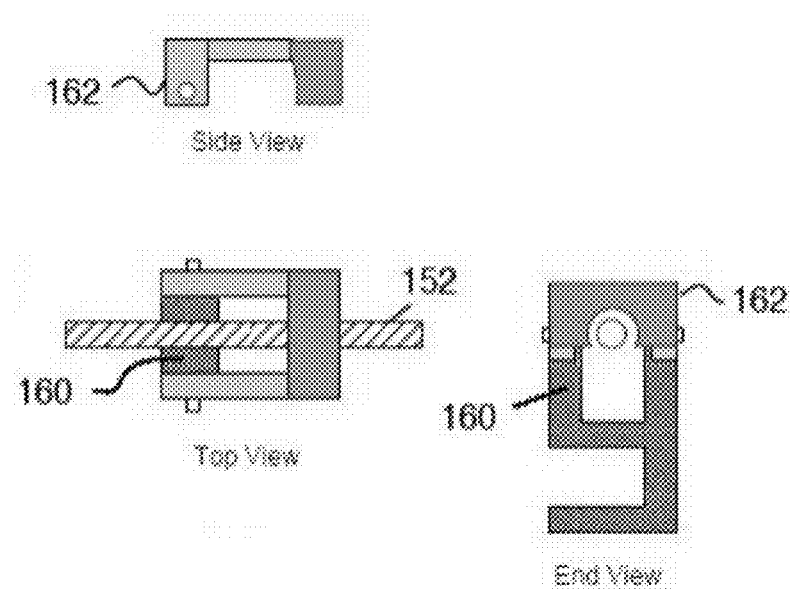
FIG. 4e is a schematic of a side view, top view, and end view of the flexion stop and extension stop in the force positions in the actuator system of the third variation.
Figure 4F:
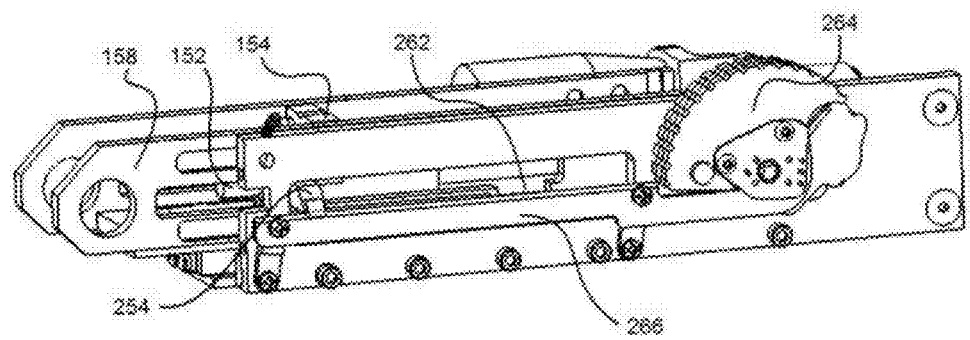
FIG. 4f is a schematic of the actuator system, with the preferred variation of the moving rail.

In a second variation, as shown in FIG. 4c, the moving rail 158 of the linear slide 156 may additionally or alternatively include a latch 262, which functions to translate linear movement of the ball nut 154 in both the flexion and extension directions into a flexion and extension of the joint. In the preferred embodiment, the latch 262 includes a flexion stop surface and an extension stop surface. Similar to the flexion stop 162 in the first variation, the flexion stop surface of the latch functions to translate linear movement of the ball nut 154 in a flexion direction into a flexion of the joint. Similar to the extension stop 160 in the first variation, the extension stop surface of the latch functions to translate linear movement of the ball nut 154 in an extension direction into an extension of the joint. The latch 262 is preferably movable between an engaged position (shown in FIG. 4c) that allows the ball nut 154 to apply force against the extension stop surface and/or flexion stop surface of the latch to move the latch 262 and the moving rail, and a disengaged position (not shown) that prevents the ball nut 154 from applying force against the latch 262. Similar to the extension stop 160 and flexion stop 162 in the force position, the latch 262 preferably applies a symmetric force to the ball nut 154 when in the engaged position, to avoid damaging or obstructing the ball nut. The latch 262, unlike the extension stop 160, is preferably mounted to engage and disengage in a slidable manner towards and away from the ball nut 154 The extension stop surface and flexion stop surface of the latch 262 preferably are sides of a rectangular side cutout 262 in the moving rail 158 (shown in FIG. 4f), into which an extended arm 254 coupled to the ball nut 154 engages and disengages in a slidable manner. The extended arm 254, which is spring-loaded to default to the engaged position, slides into the side cutout to move into the engaged position, and slides out of the side cutout to move into the disengaged position. The latch 262 is preferably selected in the engaged position or disengaged position with a knob 264 (shown in FIG. 4f) coupled to the latch with a linkage mechanism 266 that pushes the extended arm 254 into the disengaged position and releases the extended arm 254 into the engaged position. The knob 264 is preferably movable between two discrete positions, one for latch engagement and one for latch disengagement, with the use of a ball plunger pressing against two discrete indentations, positioning a pin in one of a hole corresponding to latch engagement and a hole corresponding to latch disengagement, or any suitable mechanism.

The latch 262 may alternatively engage and disengage the ball nut 154 in a pivoting manner in a direction that is lateral to the moving rail 158, or be shaped and mounted in any manner to allow movement from the engaged position to the disengaged position. The latch 262 may also alternatively be selected with a lever, manual handle, switch, an electronic switch, and/or any other suitable means of moving the latch between the engaged position and the disengaged position.

In another variation, the latch 262 is coupled to the ball nut 154 in an engaged position and free of the ball nut 154 in a disengaged position. Similar to the second variation, the latch 262 is movable between the engaged position and the disengaged position. When the latch 262 is in the engaged position, the latch 262 is coupled to the ball nut 154 such that linear movement of the nut in flexion and extension directions causes the latch 262 to move in flexion and extension directions and translate flexion and extension directions into a flexion and extension of the joint. When the latch 262 is in the disengaged position, the ball nut 154 moves independently of the latch 262 such that linear movement of the ball nut 154 does not cause the latch 262 to move.

In another variation, the flexion stop 162 and latch 262 may be omitted to allow unpowered flexion of the joint. In yet another variation, the extension stop 160 and flexion stop 162 may be omitted to allow unpowered extension and flexion of the joint.

The extension stop 160 and the flexion stop 162 are preferably located relatively far from each other, which allows the joint of the user to experience "free movement", essentially moving the moving rail 158 back and forth between the extension stop 160 and the flexion stop 162 without the need to move the ball nut 154 or back-drive the multi-motor assembly 120. In a variation, the extension stop 160 and the flexion stop 162 are located relatively close to each other, which prevents the joint of the user from experiencing little or no "free movement". In other words, movement of the moving rail 158 will move the ball nut 154 and back-drive the multi-motor assembly 120. Similar to the extension stop 160 and flexion stop 162, the extension stop surface and flexion stop surface of latch 262 are preferably located relatively far from each other, but in a variation, the extension stop surface and flexion stop surface of the latch are located relatively close to each other.

As shown in FIG. 1, the actuator system 100 of the preferred embodiments for extending and flexing a joint 110 of a user includes a rotary-to-linear mechanism that functions to convert the linear movement of the moving rail into an extension and flexion (both rotational movements) of the joint of the user. In other variations, the actuator system 100 may include gears, pulleys, or any other suitable mechanism to ultimately extend and flex the joint of the user.

3. Controller

The controller of the preferred embodiment functions to operate the actuator system 100 in one of several operation modes. The controller preferably includes sensors to estimate the position of the moving rail 158, and a sensor on the motor 129 to maintain the position of the ball nut 154. Additional sensors estimate the force either provided by the multi-motor assembly 120 (for instance, via current sensors) or the total force applied to the joint via force sensors coupled to the thrust bearings (not shown) supporting drive shaft 122. The controller may also include other sensors to predict or determine future forces applied to the joint or needed by the multi-motor assembly 120. The controller may, however, use any suitable method or device to estimate the position of the moving rail 158 and the torque required from the multi-motor assembly 120.

Figure 5:
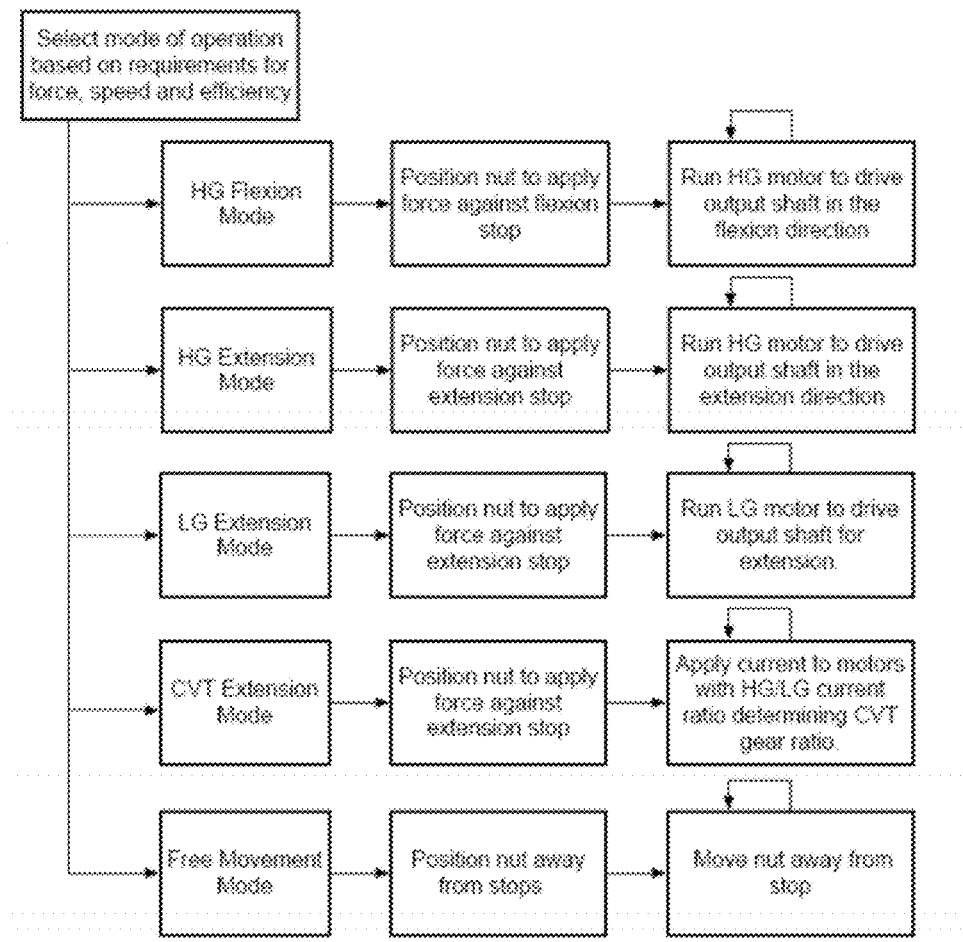
FIG. 5 is a flow diagram of the operation modes for the controller of the actuator system of the preferred embodiment.

Based on the position of the moving rail 158 and the force needed by the multi-motor assembly 120, the controller provides current to the first motor subsystem 124, the second motor subsystem 126, or both the first motor subsystem 124 and the second motor subsystem 126. As shown in FIG. 5, the controller preferably operates the multi-motor assembly 120 of the actuator system 100 in the following operation modes: High Gear Flexion mode, High Gear Extension mode, Low Gear Extension mode, and Continuously Variable Transmission Extension mode.

In the High Gear Flexion mode, the controller provides current only to the first motor subsystem 124 such that the multi-motor assembly 120 provides a rotational output to the rotary-to-linear mechanism 150. The ball screw 152 is driven in the direction such that the ball nut 154 applies a force against the flexion stop 162 (if positioned in the force position) and drives the moving rail 158 in the flexion direction. The High Gear Flexion mode supplies a smaller force at a higher speed to quickly flex the joint of the user.

The High Gear Extension mode is similar to the High Gear Flexion mode, except the first motor subsystem 124 is driven in the opposite direction. In the High Gear Extension mode, the controller provides current only to the first motor subsystem 124 such that the multi-motor assembly 120 provides a rotational output to the rotary-to-linear mechanism 150 and the ball nut 154 applies a force against the extension stop 160. The ball screw 152 is driven in the direction such that the ball nut 154 applies a force against the extension stop 160 (if positioned in the force position) and drives the moving rail 158 in the extension direction. The High Gear Extension mode supplies a smaller force at a higher speed to quickly extend the joint of the user.

The Low Gear Extension mode is similar to the High Gear Extension mode, except the second motor subsystem 126 is driven instead of the first motor subsystem 124. In the Low Gear Extension mode, the controller provides current only to the second motor subsystem 126 such that the multi-motor assembly 120 provides a rotational output to the rotary-to-linear mechanism 150 and the ball nut 154 applies a force against the extension stop 160. The ball screw 152 is driven in the direction such that the ball nut 154 applies a force against the extension stop 160 (if positioned in the force position) and drives the moving rail 158 in the extension direction. The Low Gear Extension mode supplies a larger force at a lower speed to forcefully extend the joint of the user.

Figure 6:
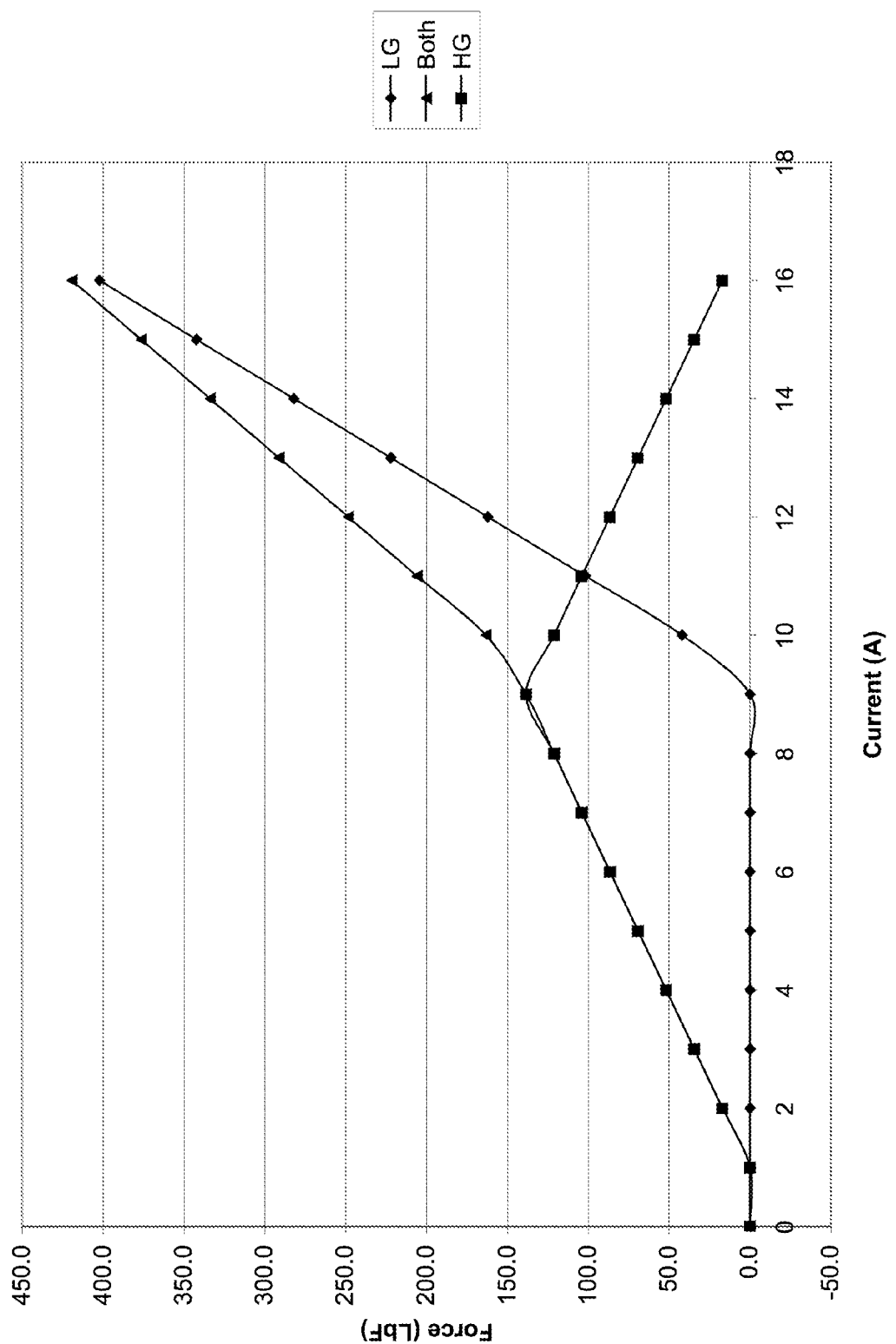
FIG. 6 is an exemplary current ramping scheme for the controller of the actuator system of the preferred embodiment.
Figure 7:
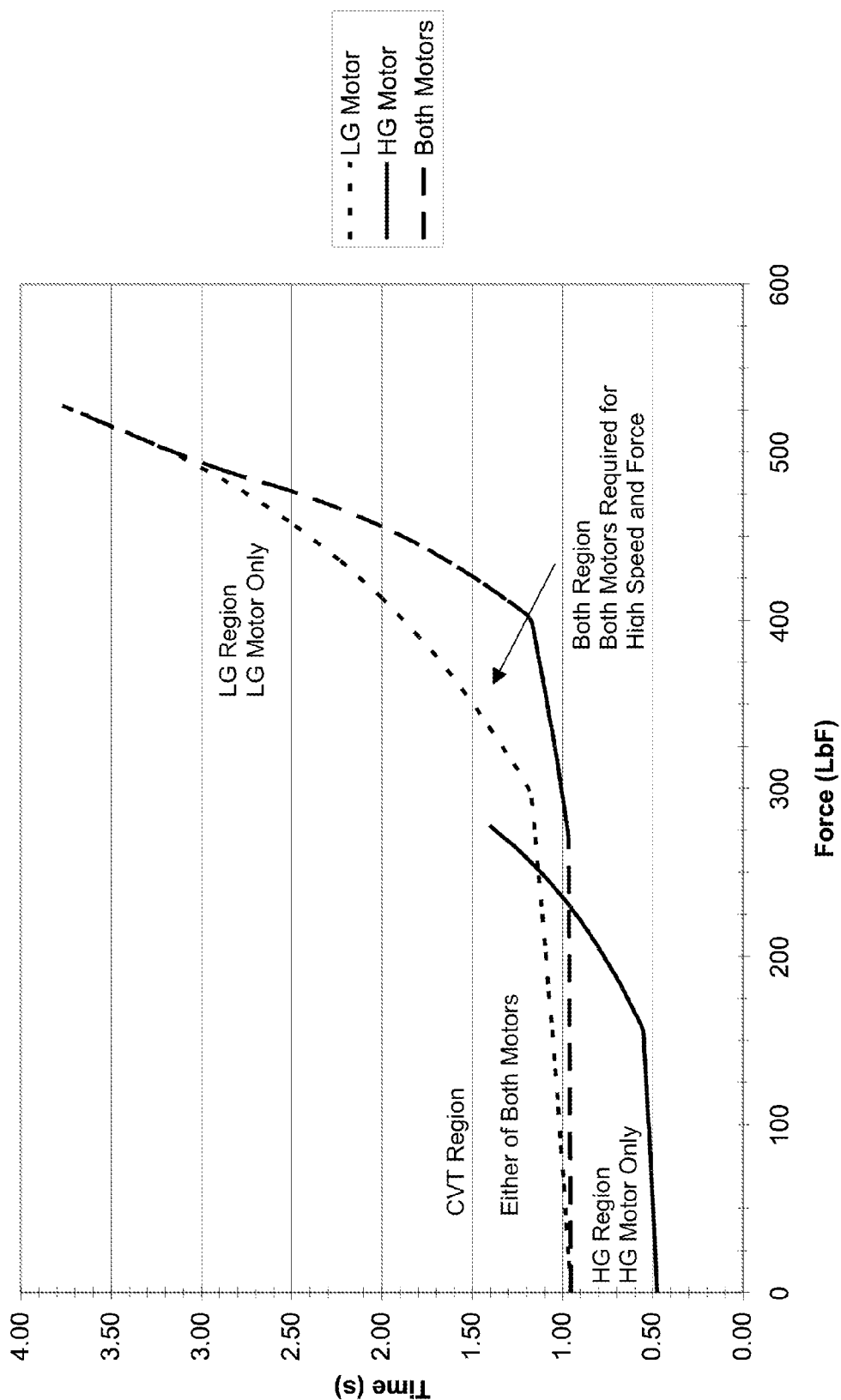
FIG. 7 is a chart of the speed/force profile of the first motor subsystem, the second motor subsystem, and the combination of the first and second motor subsystems.

In the Continuously Variable Transmission Extension mode, the controller provides current to both the first motor subsystem 124 and the second motor subsystem 126 such that the multi-motor assembly 120 provides a rotational output to the rotary-to-linear mechanism 150 and the ball nut 154 applies a force against the extension stop 160. In this mode, as exemplified in FIG. 6, the controller varies the ratio of current provided to the first motor subsystem 124 and current provided to the second motor subsystem 126 to achieve a desired rotational output in the Continuously Variable Transmission Extension mode. As the controller senses an increased force needed by the multi-motor assembly 120, the controller preferably first ramps up the current to the first motor subsystem 124 (the High Gear or "HG"), then ramps down the current to the first motor subsystem 124 while ramping up the current to the second motor subsystem 126 (the Low Gear or "LG"). The Continuously Variable Transmission Extension mode can supply both a smaller force at a higher speed to quickly extend the joint of the user ("High Gear"), and a larger force at a lower speed to forcefully extend the joint of the user ("Low Gear"). More importantly, as shown in FIG. 7, by varying the ratio of current provided to the first motor subsystem 124 and current provided to the second motor subsystem 126, the controller can achieve a desired force and speed from the multi-motor subsystem that is outside the range of possible forces and speeds supplied by just the first motor 128 or the second motor 134. The actuator system 100 provides these advantages and features without providing a conventional multi-gear transmission or conventional CTV (with gears, conical pulleys, etc.).

As shown in FIG. 5, the controller of the preferred embodiment also operates the actuator system 100 in a Free Movement mode. In one variation of the Free Movement mode, the controller provides current to the first motor subsystem 124 such that the multi-motor assembly 120 provides a rotational output to the rotary-to-linear mechanism 150 and the ball nut 154 moves away from the extension stop 160. In another variation of the Free Movement mode, the controller provides current to the first motor subsystem 124 such that the multi-motor assembly 120 provides a rotational output to the rotary-to-linear mechanism 150 and the ball nut 154 maintains a general position between—but not contacting—the extension stop 160 or the flexion stop 162.

4. Further Embodiments

As a person skilled in the art of actuator system 100s will recognize from the previous detailed description and from the figures and claims, modifications and changes can be made to the preferred embodiments of the invention without departing from the scope of this invention defined in the following claims. As a first example, while the actuator system 100 has been described to include a multi-motor assembly 120 with a first motor 128 and a second motor 134, the multi-motor assembly 120 may include additional motors (with or without additional one-way clutches 140). As an additional example, while the actuator system 100 has been described to include a rotary-to-linear mechanism 150, it is possible that the rotational output of the multi-motor assembly 120 may be used without a mechanism that converts the rotational output to a linear output.

We claim:

1. An actuator system for assisting extension of a biological joint, comprising:
    a motor assembly that provides a rotational output;
    a rotary-to-linear mechanism including a screw that accepts the rotational output of the motor assembly, and a nut that cooperates with the screw to convert rotational movement of the screw to linear movement of the nut; and
    an extension stop which is driven by linear movement of the nut in an extension direction to cause extension of the biological joint, wherein the motor assembly, the rotary-to-linear mechanism and the extension stop cooperate to allow unpowered flexion of the joint, wherein the system is configured without a flexion stop, and wherein the system is configured such that the nut cannot drive the joint in a flexion direction.

2. The actuator system of claim 1, wherein the motor assembly allows unpowered extension of the joint when the extension stop is moved by a patient in the extension direction away from the nut.

3. The actuator system of claim 1, further comprising a moving rail upon which the extension stop is mounted, the moving rail configured to move linearly in an extension direction to cause extension of the joint.

4. The actuator system of claim 3, further comprising a controller configured to sense a position of the nut or the moving rail.

5. The actuator system of claim 4, wherein the controller is configured to provide current to the motor assembly based on the sensed position of the nut or the moving rail.

6. The actuator system of claim 3, wherein the moving rail is further configured to move linearly in a flexion direction.

7. The actuator system of claim 6, wherein the motor assembly allows for back-driving of the motor assembly when the extension stop is moved against the nut by a patient in the flexion direction.

8. The actuator system of claim 1, wherein the motor assembly includes a drive shaft, and wherein the screw is connected to the drive shaft.

9. The actuator system of claim 1, wherein the nut is a ball nut.

10. An actuator system for assisting extension of a joint, comprising:
    a motor assembly that provides a rotational output;
    a rotary-to-linear mechanism including a screw that accepts the rotational output of the motor assembly, and a nut that cooperates with the screw to convert rotational movement of the screw to linear movement of the nut; and
    an extension stop which is driven by linear movement of the nut in an extension direction to cause extension of the joint, wherein the motor assembly, the rotary-to-linear mechanism and the extension stop cooperate to allow unpowered flexion of the joint,
    wherein the extension stop is movable between a force position that allows the nut to apply force against the extension stop, and a pass position that prevents the nut from applying force against the extension stop.

11. A method of assisting extension of a biological joint of a user, the method comprising:
    receiving rotational output from a motor assembly;
    translating the rotational output to linear output using a rotary-to-linear mechanism;
    assisting extension of the biological joint using the linear output from the mechanism; and
    allowing for unpowered extension of the joint,
    wherein an actuator system which comprises the motor assembly and the rotary-to-linear mechanism includes a screw that accepts the rotational output of the motor assembly, a nut that cooperates with the screw to convert rotational movement of the screw to linear movement of the nut, and an extension stop which is driven by linear movement of the nut in an extension direction, wherein the actuation system is configured without a flexion stop, and wherein the system is configured such that the nut cannot drive the joint in a flexion direction.

12. The method of claim 11, further comprising allowing unpowered flexion of the joint.

13. The method of claim 11, wherein an actuator system which comprises the motor assembly and the rotary-to-linear mechanism includes gears or pulleys.

14. The method of claim 11, wherein the extension stop is moved by the user in the extension direction away from the nut when there is unpowered extension of the joint by the user.

15. The method of claim 11, further comprising back-driving the motor assembly when the extension stop is moved against the ball nut by the user in a flexion direction.

* * * * *